(12) United States Patent
Senzaki

(10) Patent No.: US 10,336,976 B2
(45) Date of Patent: Jul. 2, 2019

(54) PHOTOSENSITIVE RESIN COMPOSITION FOR FORMING CELL CULTURE SUBSTRATE

(71) Applicant: TOKYO OHKA KOGYO CO., LTD., Kawasaki-shi (JP)

(72) Inventor: Takahiro Senzaki, Kawasaki (JP)

(73) Assignee: TOKYO OHKA KOGYO CO., LTD., Kawasaki-Shi (JP)

(*) Notice: Subject to any disclaimer, the term of this patent is extended or adjusted under 35 U.S.C. 154(b) by 170 days.

(21) Appl. No.: 15/303,930

(22) PCT Filed: Apr. 10, 2015

(86) PCT No.: PCT/JP2015/061251
§ 371 (c)(1),
(2) Date: Nov. 21, 2016

(87) PCT Pub. No.: WO2015/159821
PCT Pub. Date: Oct. 22, 2015

(65) Prior Publication Data
US 2017/0137767 A1 May 18, 2017

(30) Foreign Application Priority Data
Apr. 18, 2014 (JP) ................ 2014-086576

(51) Int. Cl.
| | | |
|---|---|---|
| *G03F 7/031* | (2006.01) | |
| *G03F 7/028* | (2006.01) | |
| *C12M 3/00* | (2006.01) | |
| *C12M 1/00* | (2006.01) | |
| *B29C 41/12* | (2006.01) | |
| *C08F 2/46* | (2006.01) | |
| *C08J 7/00* | (2006.01) | |
| *B29C 35/00* | (2006.01) | |
| *B29C 35/08* | (2006.01) | |
| *B29C 41/00* | (2006.01) | |
| *B29C 41/42* | (2006.01) | |
| *B29C 71/00* | (2006.01) | |
| *B29C 71/04* | (2006.01) | |
| *B29D 7/00* | (2006.01) | |
| *B29K 33/04* | (2006.01) | |
| *B29K 67/00* | (2006.01) | |
| *B29K 71/00* | (2006.01) | |
| *B29L 7/00* | (2006.01) | |

(52) U.S. Cl.
CPC .......... *C12M 23/20* (2013.01); *B29C 35/002* (2013.01); *B29C 35/0805* (2013.01); *B29C 41/003* (2013.01); *B29C 41/12* (2013.01); *B29C 41/42* (2013.01); *B29C 71/0009* (2013.01); *B29C 71/04* (2013.01); *B29D 7/00* (2013.01); *C08F 2/46* (2013.01); *C08J 7/00* (2013.01); *G03F 7/028* (2013.01); *G03F 7/031* (2013.01); *B29C 2035/0827* (2013.01); *B29C 2071/0045* (2013.01); *B29K 2033/04* (2013.01); *B29K 2067/06* (2013.01); *B29K 2071/00* (2013.01); *B29L 2007/00* (2013.01)

(58) Field of Classification Search
CPC ........ G03F 7/0037; G03F 7/028; G03F 7/031; B29C 41/003; B29C 41/12; B29C 41/42; B29C 2035/0827; C12M 23/20; C12M 23/26
USPC ............................................. 430/288.1, 320
See application file for complete search history.

(56) References Cited

U.S. PATENT DOCUMENTS

| | | |
|---|---|---|
| 2002/0171176 A1 | 11/2002 | Hanna |
| 2006/0228386 A1* | 10/2006 | Stephens ............... B29C 39/006 424/401 |
| 2008/0220526 A1 | 9/2008 | Ellison et al. |
| 2009/0098651 A1 | 4/2009 | Watanabe |
| 2009/0170190 A1 | 7/2009 | Nishi et al. |
| 2009/0191627 A1 | 7/2009 | Fadeev et al. |
| 2009/0191634 A1 | 7/2009 | Martin et al. |
| 2010/0286300 A1 | 11/2010 | Hanabata |

(Continued)

FOREIGN PATENT DOCUMENTS

| | | |
|---|---|---|
| EP | 2863245 | 4/2015 |
| JP | 2003-010312 | 1/2003 |

(Continued)

OTHER PUBLICATIONS

Partial supplementary European search report issued in European Patent Application No. 15779517.0, dated Nov. 8, 2017.

(Continued)

*Primary Examiner* — John A McPherson
(74) *Attorney, Agent, or Firm* — Knobbe, Martens, Olson & Bear LLP

(57) ABSTRACT

A photosensitive resin composition for cell culture substrates that enables the low-cost manufacture of a cell culture substrate, that can easily form patterns of various shapes when providing a pattern on the surface of a cell culture substrate, has low cytotoxicity, and that can form a cell culture substrate; a cell culture substrate that is formed using the photosensitive resin composition; and a cell culture substrate manufacturing method that uses the photosensitive resin composition. The photosensitive resin composition includes a photopolymerizable monomer and a photopolymerization initiator. The photopolymerizable monomer contains a defined amount of a polyfunctional monomer that is at least trifunctional, and the content of the photopolymerization initiator is within a prescribed range.

15 Claims, No Drawings

(56) References Cited

U.S. PATENT DOCUMENTS

| | | |
|---|---|---|
| 2011/0268948 A1 | 11/2011 | Ikuta et al. |
| 2014/0037900 A1 | 2/2014 | Takihara et al. |
| 2014/0099243 A1* | 4/2014 | Kotera ............... G03F 7/038 422/552 |
| 2014/0127463 A1 | 5/2014 | Otani et al. |
| 2015/0133566 A1 | 5/2015 | Gong et al. |

FOREIGN PATENT DOCUMENTS

| | | |
|---|---|---|
| JP | 2009-038981 | 2/2009 |
| JP | 2009-186773 A | 8/2009 |
| JP | 2009-278960 | 12/2009 |
| JP | 2010-104285 | 5/2010 |
| JP | 2010-520765 | 6/2010 |
| JP | 2010-183974 | 8/2010 |
| JP | 2011-072297 | 4/2011 |
| JP | 2011-514145 | 5/2011 |
| JP | 2011-212953 | 10/2011 |
| JP | 2011-215270 | 10/2011 |
| JP | 2012-008205 | 1/2012 |
| JP | 2012-090587 | 5/2012 |
| JP | 2013-029828 | 2/2013 |
| JP | 2014-065853 | 4/2014 |
| JP | 2014-077040 | 5/2014 |
| WO | WO 2007/105418 | 9/2007 |
| WO | WO 2009/069557 | 6/2009 |
| WO | WO 2012/141238 | 10/2012 |
| WO | WO 2013/172292 | 11/2013 |
| WO | WO 2013/005769 | 2/2015 |

OTHER PUBLICATIONS

Pedron, et al., Bioapplications of Networks Based on Photo-Cross-Linked Hyperbranched Polymers, Macromolecular Symposia, 2010, 291-292, 307-313.

Pedron, et al., Using hyperbranched macromers as crosslinkers of methacrylic networks prepared by photopolymerization, Journal of Photochemistry and Photobiology A: Chemistry, 2008, 07. 11, 200, 126-140.

* cited by examiner

PHOTOSENSITIVE RESIN COMPOSITION FOR FORMING CELL CULTURE SUBSTRATE

This application is the U.S. National Phase under 35 U.S.C. § 371 of International Application PCT/JP2015/061251, filed Apr. 10, 2015, designating the U.S., and published in Japanese as WO 2015/159821 on Oct. 22, 2015, which claims priority to Japanese Patent Application No. 2014-086576, filed Apr. 18, 2014, the entire contents of which are incorporated herein by reference.

TECHNICAL FIELD

The present invention relates to a photosensitive resin composition for forming a cell culture substrate, a cell culture substrate formed by using the photosensitive resin composition, and a method for manufacturing a cell culture substrate using the photosensitive resin composition.

BACKGROUND ART

Conventionally, various resin materials have been employed as materials for a cell culture substrate for culturing animal cells and the like because of its advantages of being light-weight and easy to be processed. Such a cell culture substrate made of resin may be often surface-treated with various materials such as a cell adhesion factor, for the purpose of, for example, improving cell culturing efficiency.

As such a cell culture substrate made of resin, for example, a cell culture substrate made of material including polymethoxy ethyl acrylate (A) and poly N-isopropyl acrylamide (B) as a base, in particular, a cell culture substrate to be suitably used for culturing a macrophage cell differentiated from human peripheral blood monocyte has been proposed (see, Patent Document 1).

Furthermore, a cell culture substrate having a pattern of fine protrusions formed by methods such as sand blasting and vapor deposition on the surface of a base plate that has been formed by injection molding acrylic resin (see, Example of Patent Document 2), and a cell culture substrate formed by thermal press molding or injection molding acrylic resin (see, Example of Patent Document 3) have been proposed.

Patent Document 1: Japanese Unexamined Patent Application, Publication No. 2011-072297
Patent Document 2: PCT International Publication No. WO2007/105418
Patent Document 3: Japanese Unexamined Patent Application, Publication No. 2012-090587

DISCLOSURE OF THE INVENTION

Problems to be Solved by the Invention

However, as in a cell culture substrate described in Patent Document 1, when a polymer obtained by photo-polymerizing a monofunctional acrylate-based monomer in the presence of a photopolymerization initiator is used as a material for a cell culture substrate, cells may not favorably be cultured under the influence of cytotoxicity of the material for the cell culture substrate.

Next, the cell culture substrate described in Example of Patent Document 2 has the following problems. Firstly, since an injection-molding device and a die to be used for injection molding are expensive, a cell culture substrate manufactured by injection molding is disadvantageous in terms of manufacturing cost. Therefore, in the cell culture substrate described in Example of Patent Document 2, production in a small lot is difficult from the viewpoint of cost. Furthermore, since it is difficult to form various types of dies from the viewpoint of cost, it is difficult to variously change the shapes of the pattern to be formed on the surface of the cell culture substrate.

Furthermore, the cell culture substrate generally has a thin flat shape. In Example of Patent Document 2, a substrate for cell culture substrate is formed by injection molding; however, in general, in molding by injection molding of a thin molded product, a problem of short shot, in which resin is not completely filled in the die, is likely to occur. The problem of short shot may be solved by increasing injection pressure; however, in this case, flash is likely to occur in a molded product. Removing flash occurring in a small molded product requires much time and labor and is not easy.

In addition, a method described in Example of Patent Document 2 has a problem that the pattern formation on the surface of the cell culture substrate requires complicated steps such as vapor deposition and sand blasting.

The cell culture substrate described in Example of Patent Document 3 has problems similar to those in Patent Document 2 in the case where the cell culture substrate is formed by injection molding, and also has the following problems in the case where the cell culture substrate is formed by thermal press molding. Firstly, a mold to be used in thermal press molding is also very expensive, similar to a die to be used in injection molding. Therefore, the cell culture substrate to be formed by thermal press molding described in Example of Patent Document 3 is disadvantageous in terms of manufacturing cost. Therefore, the cell culture substrate to be formed by thermal press molding described in Example of Patent Document 3 has problems that production in a small lot is difficult, and the pattern shape on the surface of the cell culture substrate is limited.

Furthermore, the cell culture substrate to be formed by thermal press molding described in Example of Patent Document 3 has also problems that it takes long time to cool down the cell culture substrate after pressing, and it is difficult to form a fine pattern having a width of less than 100 μm.

The present invention has been made considering the above-mentioned problems, and has an object to provide a photosensitive resin composition for forming a cell culture substrate capable of manufacturing a cell culture substrate at a low cost, capable of easily forming patterns in various shapes when providing a pattern on the surface of the cell culture substrate, having low cytotoxicity, and capable of forming a cell culture substrate with which cells can be favorably cultured. The present invention has another object to provide a cell culture substrate formed by using the above-mentioned photosensitive resin composition. The present invention has still another object to provide a method for manufacturing a cell culture substrate, using the above-mentioned photosensitive resin composition.

Means for Solving the Problems

The present inventors have found that the above-mentioned problems can be solved by a photosensitive resin composition including a photopolymerizable monomer (A) and a photopolymerization initiator (B), in which the photopolymerizable monomer (A) includes a specific amount of a polyfunctional monomer (A1) having tri- or more-functionality, and the content of the photopolymerization initiator (B) is within a predetermined range, and, thereby, have completed the present invention.

A first aspect of the present invention is a photosensitive resin composition including a photopolymerizable monomer (A) and a photopolymerization initiator (B),
wherein the photopolymerizable monomer (A) includes 10% by mass or more of a polyfunctional monomer (A1) having tri- or more-functionality in relation to a mass of the photopolymerizable monomer (A), and
the content of the photopolymerization initiator (B) is 0.5 to 5.0% by mass in relation to a mass of the photosensitive resin composition.

A second aspect of the present invention is a cell culture substrate formed by using the photosensitive resin composition for forming a cell culture substrate in accordance with the first aspect.

A third aspect of the present invention is a method for manufacturing a cell culture substrate, the method including: applying a photosensitive resin composition for forming a cell culture substrate in accordance with the first aspect so as to form a coating film on a base plate, and
exposing the coating film to light so as to cure the coating film.

Effects of the Invention

The present invention can provide a photosensitive resin composition for forming a cell culture substrate capable of manufacturing a cell culture substrate at a low cost, capable of easily forming patterns of various shapes when providing a pattern on the surface of the cell culture substrate, having low cytotoxicity, and capable of forming a cell culture substrate with which cells can be favorably cultured; a cell culture substrate using the above-mentioned photosensitive resin composition; and a method for manufacturing a cell culture substrate, using the above-mentioned photosensitive resin composition.

PREFERRED MODE FOR CARRYING OUT THE INVENTION

<<Photosensitive Resin Composition for Forming Cell Culture Substrate>>

A photosensitive resin composition for forming a cell culture substrate (hereinafter, also simply referred to as a "photosensitive resin composition") includes a photopolymerizable monomer (A) and a photopolymerization initiator (B). Furthermore, the photopolymerizable monomer (A) includes 10% by mass or more of a polyfunctional monomer (A1) having tri- or more-functionality in relation to a mass of the photopolymerizable monomer (A). In addition, the content of the photopolymerization initiator (B) in the photosensitive resin composition is 0.5 to 5.0% by mass in relation to a mass of the photosensitive resin composition.

The photosensitive resin composition for forming a cell culture substrate of the present invention has the above-mentioned specific composition, and can therefore form a cell culture substrate having low cytotoxicity and capable of favorably culturing cells. Furthermore, use of the photosensitive resin composition for forming a cell culture substrate of the present invention enables a cell culture substrate to be formed by photo-curing, and therefore, a cell culture substrate can be formed at a low cost without using expensive equipment as in injection molding or thermal press molding.

Shapes of the cell culture substrate formed by using the photosensitive resin composition are not particularly limited. The cell culture substrate formed by using the photosensitive resin composition may be a shape having a flat cell culture surface, and may be a shape having a cell culture surface provided with a concave-convex pattern. A method for forming the concave-convex pattern on the cell culture substrate will be described later.

When the cell culture substrate provided with a concave-convex pattern is formed by a method such as injection molding and thermal press molding, an expensive mold or die, which is made of a metal material resistant to high temperature molding conditions, and precisely machined, is necessary. In such cases, since the mold or die is expensive, it is difficult to produce a cell culture substrate in a small lot, and a pattern shape on the surface of the cell culture substrate is limited.

However, when the photosensitive resin composition for forming a cell culture substrate of the present invention is used, a cell culture substrate can be formed by photo-curing. When the concave-convex pattern is formed on the cell culture substrate by using the photosensitive resin composition for forming a cell culture substrate of the present invention, a mold made of an organic material such as a photocurable resin composition that is inexpensive and easily processed can be used. Consequently, the use of the photosensitive resin composition for forming a cell culture substrate of the present invention enables various cell culture substrates to be manufactured at a low cost and easily even when concave-convex patterns are variously changed.

Hereinafter, components included in the photosensitive resin composition, and a method for manufacturing the photosensitive resin composition are described in order. Note here that in the description of the photopolymerizable monomer (A), "EO" denotes ethylene oxide, and "PO" denotes propylene oxide.

[Photopolymerizable Monomer (A)]

A photopolymerizable monomer (A) is not particularly limited as long as it is a photopolymerizable monomer, and can be selected from various photopolymerizable compounds that have been conventionally used for a photosensitive resin composition. As the photopolymerizable monomer (A), from the viewpoint of preservation stability and the like of the photosensitive resin composition, a compound having an ethylenically unsaturated bond is preferable. Preferable examples of the photopolymerizable functional group included in the compound having an ethylenically unsaturated bond include a (meth)acryloyl group, a vinyl group, an allyl group, and the like. Examples of the compound having an ethylenically unsaturated bond include (meth)acrylate compounds, (meth)acrylamide compound, vinyl compound, and allyl compound respectively having mono-, bi-, tri- or more-functionality.

The photopolymerizable monomer (A) includes 10% by mass or more of a polyfunctional monomer (A1) having tri- or more-functionality in relation to the mass of the photopolymerizable monomer (A). The content of the polyfunctional monomer (A1) in the photopolymerizable monomer (A) is more preferably 10 to 30% by mass and particularly preferably 15 to 25% by mass. Use of the photopolymerizable monomer (A) including such an amount of polyfunctional monomer (A1) enables a photosensitive resin composition to be obtained, and the photosensitive resin composition is capable of forming a cell culture substrate that can favorably culture cells.

It is estimated that cytotoxicity of a cell culture substrate made of resin is attributable in part to a very small amount of monomer or oligomer included in the cell culture substrate. It is assumed that when the photosensitive resin composition includes a predetermined amount of polyfunctional monomer (A1), the polyfunctional property of the polyfunctional monomer (A1) can reduce the amount of monomer or oligomer in the cured photosensitive resin composition after the photosensitive resin composition is cured by exposure to light, and, therefore, use of the photopolymerizable monomer (A) including the polyfunctional monomer (A1) can form a cell culture substrate capable of favorably culturing cells.

Furthermore, the use of such an amount of the photopolymerizable monomer (A) including the polyfunctional monomer (A1) can suppress dissolution of the cell culture substrate into a rinse solution when the cell culture substrate formed using the photosensitive resin composition is rinsed with a solvent.

When the photopolymerizable monomer (A) is a compound having an ethylenically unsaturated bond, the polyfunctional monomer (A1) is not particularly limited as long as it is a compound having three or more ethylenically unsaturated bonds, and it does not hinder the object of the present invention. The number of the ethylenically unsaturated bonds of the polyfunctional monomer (A1) having the ethylenically unsaturated bond is 3 or more, and preferably 3 to 6.

Preferable examples of the polyfunctional monomer (A1) having an ethylenically unsaturated bond include tri- or more-functional acrylate such as trimethylolpropane tri(meth)acrylate, pentaerythritol tetra(meth)acrylate, ethylene oxide-modified pentaerythritol tetra(meth)acrylate, propylene oxide-modified pentaerythritol tetra(meth)acrylate, dipentaerythritol penta(meth)acrylate, and dipentaerythritol hexa(meth)acrylate; polyfunctional urethane(meth)acrylate obtained by reacting a polyisocyanate compound and a hydroxy group-containing (meth)acrylate monomer to each other; and a condensed product of polyvalent alcohol and N-methylol(meth)acrylamide. These polyfunctional monomers (A1) can be used alone or in combination of two or more thereof.

It is preferable that the photopolymerizable monomer (A) includes a bifunctional monomer (A2) at the content of 20% by mass or more in relation to the mass of the photopolymerizable monomer (A), in addition to the above-mentioned polyfunctional monomer (A1) having tri- or more-functionality. The content of the bifunctional monomer (A2) in the photopolymerizable monomer (A) is preferably 40 to 90% by mass, and particularly preferably 50 to 90% by mass. When the polyfunctional monomer (A1) is a compound having an ethylenically unsaturated bond, a compound having two ethylenically unsaturated bonds is used as the bifunctional monomer (A2).

For example, when the photopolymerizable monomer (A) includes the below-mentioned monofunctional monomer (A3) and the polyfunctional monomer (A1), after the photosensitive resin composition is cured by exposure to light, the monofunctional monomer (A3) may tend to remain slightly in the cured product. Furthermore, when the photopolymerizable monomer (A) includes more than 90% by mass of the polyfunctional monomer (A1), when the photosensitive resin composition is cured by exposure to light, since the cross-linked density of the cured product becomes excessively high, radical polymerization does not proceeds smoothly, and photopolymerizable monomers (A) may tend to remain slightly in the cured product.

However, when the photopolymerizable monomer (A) includes the above-mentioned amount of the bifunctional monomer (A2) in addition to the aforementioned amount of the polyfunctional monomer (A1), it is possible to allow the radical polymerization of the photopolymerizable monomer (A) to favorably proceed, and to suppress remaining of the photopolymerizable monomer (A) in the cured product obtained by curing the photosensitive resin composition by exposure to light.

Among the bifunctional monomers (A2) having an ethylenically unsaturated bond, a compound expressed in the following formula 1 is preferable:

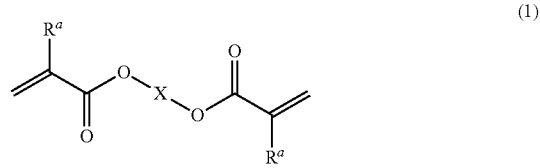

(in the formula 1, $R^a$ each independently represents a hydrogen atom, or an alkyl group having 1 to 5 carbon atoms; X represents a divalent group expressed in the following formula 2:

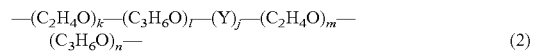

wherein Y represents a group selected from divalent groups expressed in the following formulae Y1 to Y3:

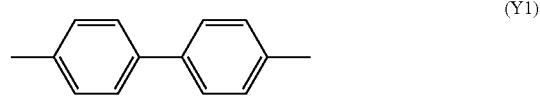

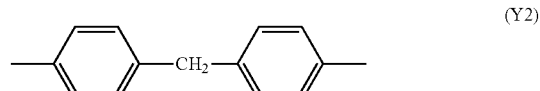

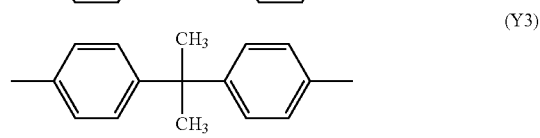

k, l, m, and n each independently represents an integer of 0 or more; a sum of k, l, m, and n is an integer of 2 to 6; and j represents an integer of 0 or 1.

Use of the bifunctional monomer (A2) expressed in the above-mentioned formula 1 allows for obtaining a photosensitive resin composition capable of forming a cell culture substrate having appropriate flexibility and mechanical strength.

Furthermore, as the bifunctional monomer (A2), compounds other than the compound expressed in the above-mentioned formula 1 can be used. Examples of the bifunctional monomer (A2) that can be used as the compounds other than the compound expressed in the above-mentioned formula 1 include polyethylene glycol di(meth)acrylate, polypropylene glycol di(meth)acrylate, polyethylene polypropylene glycol di(meth)acrylate, ethylene glycol di(meth)acrylate, propylene glycol di(meth)acrylate, polyethylene polytrimethylolpropane di(meth)acrylate, 2-(meth)acryloyloxy-2-hydroxypropylphthalate, 2-(meth)acryloyloxyethyl-2-hydroxyethyl phthalate, a compound obtained by allowing a glycidyl group-containing compound to react with α,β-unsaturated carboxylic acid, urethane monomer, γ-chloro-β-hydroxypropyl-β'-(meth)acryloyloxy  ethyl-o-phthalate, β-hydroxyethyl-β'-(meth)acryloyloxy ethyl-o-phthalate, and β-hydroxypropyl-β'-(meth)acryloyloxy ethyl-o-phthalate, and the like.

Examples of the compound obtained by allowing a glycidyl group-containing compound to react with α,β-unsaturated carboxylic acid include triglycerol di(meth)acrylate, and the like. Examples of the above-mentioned urethane monomer include an addition reaction product of a (meth)acrylic monomer having a hydroxyl group at β position with isophorone diisocyanate, 2,6-toluene diisocyanate, 2,4-toluene diisocyanate, 1,6-hexamethylene diisocyanate, and the like, EO-modified urethane di(meth)acrylate, and EO- and PO-modified urethane di(meth)acrylate, and the like.

The content of the compound expressed in the above-mentioned formula 1 in the bifunctional monomer (A2) is not particularly limited; however, the content is preferably 50% by mass or more, more preferably 60% by mass or more, and particularly preferably 80% by mass or more.

The photopolymerizable monomer (A) may include the monofunctional monomer (A3); however, from the viewpoint that a cured product having low cytotoxicity is easily formed, it is preferable that the photopolymerizable monomer (A) does not include the monofunctional monomer (A3). The content of the monofunctional monomer (A3) in the photopolymerizable monomer (A) is preferably 25% by mass or less, and more preferably 20% by mass or less. When the polyfunctional monomer (A1) is a compound having an ethylenically unsaturated bond, a compound having one ethylenically unsaturated bond is used as the monofunctional monomer (A3).

Examples of the compound having an ethylenically unsaturated bond that can be preferably used as the monofunctional monomer (A3) include (meth)acrylic acid esters, (meth)acrylamides, an allyl compound, vinyl ethers, vinyl esters, styrenes, and the like. These compounds can be used alone or in combination of two or more thereof.

Examples of the (meth)acrylic acid esters include methyl (meth)acrylate, ethyl(meth)acrylate, propyl(meth)acrylate, amyl(meth)acrylate, t-octyl(meth)acrylate, chloroethyl (meth)acrylate, 2,2-dimethyl hydroxypropyl(meth)acrylate, 2-hydroxyethyl (meth)acrylate, trimethylol propane mono (meth)acrylate, benzyl(meth)acrylate, furfuryl(meth)acrylate, phenyl(meth)acrylate, EO adduct of phenol(meth)acrylate, PO adduct of phenol(meth)acrylate, EO/PO co-adduct of phenol(meth)acrylate, ethylene glycol mono(meth)acrylate, diethylene glycol mono(meth)acrylate, triethylene glycol mono(meth)acrylate, polyethylene glycol mono(meth)acrylate, 2-methoxyethyl(meth)acrylate, diethylene glycol monomethyl ether mono(meth)acrylate, triethylene glycol monomethyl ether mono(meth)acrylate, polyethylene glycol monoethyl ether mono(meth)acrylate, propylene glycol mono(meth)acrylate, dipropylene glycol mono(meth)acrylate, tripropylene glycol mono(meth)acrylate, polypropylene glycol mono(meth)acrylate, propylene glycol monomethyl ether mono(meth)acrylate, dipropylene glycol monomethyl ether mono(meth)acrylate, tripropylene glycol monomethyl ether mono(meth)acrylate, polypropylene glycol monomethyl ether mono(meth)acrylate, mono(meth)acrylate of an EO/PO copolymer, monomethyl ether mono (meth)acrylate of an EO/PO copolymer, and the like.

Examples of the (meth)acrylamides include (meth)acrylamide, N-alkyl(meth)acrylamide, N-aryl(meth)acrylamide, N,N-dialkyl(meth)acrylamide, N,N-aryl(meth)acrylamide, N-methyl-N-phenyl(meth)acrylamide, N-hydroxyethyl-N-methyl(meth)acrylamide, and the like.

Examples of the allyl compound include allyl esters such as allyl acetate, allyl caproate, allyl caprylate, allyl laurate, allyl palmitate, allyl stearate, allyl benzoate, allyl acetoacetate, and allyl lactate; allyloxyethanol; and the like.

Examples of the vinyl ethers include alkyl vinyl ethers such as hexyl vinyl ether, octyl vinyl ether, decyl vinyl ether, ethylhexyl vinyl ether, methoxyethyl vinyl ether, ethoxy ethyl vinyl ether, chloroethyl vinyl ether, 1-methyl-2,2-dimethyl propyl vinyl ether, 2-ethyl butyl vinyl ether, hydroxyethyl vinyl ether, diethylene glycol vinyl ether, dimethylamino ethyl vinyl ether, diethyl amino ethyl vinyl ether, butyl amino ethyl vinyl ether, benzyl vinyl ether, and tetrahydrofurfuryl vinyl ether; vinyl aryl ethers such as vinyl phenyl ether, vinyl tolyl ether, vinyl chlorophenyl ether, vinyl-2,4-dichlorophenyl ether, vinyl naphthyl ether, and vinyl anthranil ether, and the like.

Examples of vinyl esters include vinyl butyrate, vinyl isobutyrate, vinyl trimethylacetate, vinyl diethylacetate, vinyl valeate, vinyl caproate, vinyl chloroacetate, vinyl dichloroacetate, vinyl methoxyacetate, vinyl butoxyacetate, vinyl phenylacetate, vinyl acetoacetate, vinyl lactate, vinyl-β-phenylbutyrate, vinyl benzoate, vinyl salicylate, vinyl chlorobenzoate, vinyl tetrachlorobenzoate, vinyl naphthoate, and the like.

Examples of styrenes include styrene; alkyl styrene such as methylstyrene, dimethylstyrene, trimethylstyrene, ethylstyrene, diethylstyrene, isopropylstyrene, butylstyrene, hexylstyrene, cyclohexylstyrene, decylstyrene, benzylstyrene, chloromethylstyrene, trifluoromethylstyrene, ethoxymethylstyrene, and acetoxymethylstyrene; alkoxystyrene such as methoxystyrene, 4-methoxy-3-methylstyrene, and dimethoxystyrene; halostyrene such as chlorostyrene, dichlorostyrene, trichlorostyrene, tetrachlorostyrene, pentachlorostyrene, bromostyrene, dibromostyrene, iodostyrene, fluorostyrene, trifluorostyrene, 2-bromo-4-trifluoromethylstyrene and 4-fluoro-3-trifluoromethylstyrene; and the like.

It is preferable that the photopolymerizable monomer (A) is a monomer made of the polyfunctional monomer (A1) and the bifunctional monomer (A2) among the above-mentioned monomers. When the photopolymerizable monomer (A) is made of the polyfunctional monomer (A1) and the bifunctional monomer (A2), the ratio of the mass of the polyfunctional monomer (A1) to the mass of the bifunctional monomer (A2) (the mass of the polyfunctional monomer (A1)/the mass of the bifunctional monomer (A2)) is preferably 10/90 to 80/20, and more preferably 15/85 to 70/30.

[Photopolymerization Initiator (B)]

A photosensitive resin composition includes 0.5 to 5.0% by mass, and more preferably 1.0 to 4.0% by mass of the photopolymerization initiator (B) in relation to the mass of the photosensitive resin composition. When the photosensitive resin includes such an amount of photopolymerization initiator (B), it is possible to reduce the cytotoxicity caused by the residual monomer of the cured product obtained by curing by exposure of the photosensitive resin composition and the photopolymerization initiator (B).

The photopolymerization initiator (B) is appropriately selected from conventionally used photopolymerization initiators according to the types of photopolymerizable monomers (A) within a scope in which the objects of the present invention are not impaired. Examples of the preferable photopolymerization initiator (B) using the photopolymerizable monomer (A) having an ethylenically unsaturated bond include 1-hydroxycyclohexyl phenyl ketone, 2-hydroxy-2-methyl-1-phenylpropan-1-one, 1-[4-(2-hydroxy ethoxy)phenyl]-2-hydroxy-2-methyl-1-propan-1-one, 1-(4-isopropylphenyl)-2-hydroxy-2-methylpropan-1-one, 1-(4-dodecylphenyl)-2-hydroxy-2-methylpropan-1-one, 2,2-dimethoxy-1,2-diphenylethan-1-one, bis(4- dimethylaminophenyl) ketone, 2-methyl-1-[4-(methylthio) phenyl]-2-morpholinopropan-1-one, 2-benzyl-2-dimethylamino-1-(4-morpholinophenyl)-butan-1-one, ethanone,1-[9-ethyl-6-(2-methyl benzoyl)-9H-carbazol-3-yl], 1-(o-acetyloxime), 2,4,6-trimethylbenzoyldiphenyl-phosphine oxide, 4-benzoyl-4'-methyldimethylsulfide, 4-dimethylaminobenzoic acid, 4-dimethylaminobenzoic acid methyl, 4-dimethylaminobenzoic acid ethyl, 4-dimethylaminobenzoic acid butyl, 4-dimethylamino-2-ethyl hexyl benzoic acid, 4-dimethylamino-2-isoamyl benzoic acid, benzyl-β-methoxyethyl acetal, benzyl dimethyl ketal, 1-phenyl-1,2-propanedione-2-(o-ethoxy carbonyl)oxime, o-benzoyl benzoic acid methyl, 2,4-diethyl thioxanthone, 2-chlorothioxanthone, 2,4-dimethylthioxanthone, 1-chloro-4-propoxy thioxanthone, thioxanthene, 2-chlorothioxanthene, 2,4-diethyl thioxanthene, 2-methylthioxanthene, 2-isopropyl thioxanthene, 2-ethyl anthraquinone, octamethyl anthraquinone, 1,2-benzanthraquinone, 2,3-diphenyl anthraquinone, azobisisobutyronitrile, benzoyl peroxide, cumene peroxide, 2-mercapto benzimidazole, 2-mercapto benzoxazole, 2-mercaptobenzothiazole, 2-(o-chlorophenyl)-4,5-di(m-methoxyphenyl)-imidazolyl dimer, benzophenone, 2-chlorobenzophenone, p,p'-bisdimethylamino benzophenone, 4,4'-bisdiethylamino benzophenone, 4,4'-dichlorobenzophenone, 3,3-dimethyl-4-methoxybenzophenone, benzyl, benzoin, benzoin methyl ether, benzoin ethyl ether, benzoinisopropyl ether, benzoin-n-butyl ether, benzoin isobutyl ether, benzoin butyl ether, acetophenone, 2,2-diethoxy acetophenone, p-dimethyl acetophenone, p-dimethylamino propiophenone, dichloroacetophenone, trichloroacetophenone, p-tert-butylacetophenone, p-dimethylamino acetophenone, p-tert-butyltrichloroacetophenone, p-tert-butyldichloroacetophenone, α,α-dichloro-4-phenoxyacetophenone, thioxanthone, 2-methylthioxanthone, 2-isopropyl thioxanthone, dibenzosuberone, pentyl-4-dimethylamino benzoate, 9-phenyl acridine, 1,7-bis-(9-acridinyl)heptane, 1,5-bis-(9-acridinyl)pentane, 1,3-bis-(9-acridinyl)propane, p-methoxytriazine, 2,4,6-tris(trichloromethyl)-s-triazine, 2-methyl-4,6-bis(trichloromethyl)-s-triazine, 2-[2-(5-methylfuran-2-yl)ethenyl]-4,6-bis(trichloromethyl)-s-triazine, 2-[2-(furan-2-yl)ethenyl]-4,6-bis(trichloromethyl)-s-triazine, 2-[2-(4-diethylamino-2-methyl phenyl)ethenyl]-4,6-bis(trichloromethyl)-s-triazine, 2-[2-(3,4-dimethoxyphenyl)ethenyl]-4,6-bis(trichloromethyl)-s-triazine, 2-(4-methoxyphenyl)-4,6-bis(trichloromethyl)-s-triazine, 2-(4-ethoxy styryl)-4,6-bis(trichloromethyl)-s-triazine, 2-(4-n-butoxy phenyl)-4,6-bis(trichloromethyl)-s-triazine, 2,4-bis-trichloromethyl-6-(3-bromo-4-methoxy)phenyl-s-triazine, 2,4-bis-trichloromethyl-6-(2-bromo-4-methoxy)phenyl-s-triazine, 2,4-bis-trichloromethyl-6-(3-bromo-4-methoxy) styryl phenyl-s-triazine, 2,4-bis-trichloromethyl-6-(2-bromo-4-methoxy)styryl phenyl-s-triazine, and the like. Among them, from the viewpoint that the cytotoxicity of a cell culture substrate formed by using a photosensitive resin composition is low, a photopolymerization initiator selected from α-aminoalkylphenone-based photopolymerization initiator and oxime ester photopolymerization initiator is preferable. Those photopolymerization initiators (B) can be used alone or in combination of two or more thereof.

[Other Components (C)]

A photosensitive resin composition can contain additives such as a solvent, a surface-active agent, an adhesion improving agent, a thermal polymerization inhibitor, and a defoaming agent, if necessary, in addition to the photopolymerizable monomer (A) and the photopolymerization initiator (B). For any of the additives, conventionally well-known additives can be used. Examples of the surface-active agent include anionic, cationic, nonionic compounds, and the like; examples of the adhesion improving agents include conventionally well-known silane coupling agents; examples of the thermal polymerization inhibitors include hydroquinone, hydroquinone monoethyl ether, and the like; examples of the defoaming agent include silicone compounds, fluorine compounds, and the like.

When a mold formed on a base plate by using a photoresist composition in order to form a cell culture substrate, when a photosensitive resin composition includes, for example, a large amount of good solvent, such as propylene glycol-1-methyl ether acetate (PGMEA), in relation to the resin material constituting a mold, the base plate serving as the mold may be damaged by the solvent. In this case, the photosensitive resin composition that does not include a solvent is preferable. When the photosensitive resin composition contains a good solvent in relation to the resin material constituting the mold as a solvent, the content of the solvent in the photosensitive resin composition is preferably 5% by mass or less in relation to the mass of photosensitive resin composition. Preferable examples of the solvent to be blended in the photosensitive resin composition include aliphatic hydrocarbon such as hexane, heptane, octane, decane, and cyclohexane; and alcohols such as methanol, ethanol, 1-propanol, 2-propanol, and 1-butanol.

[Method for Manufacturing Photosensitive Resin Composition]

A photosensitive resin composition can be prepared by mixing (dispersing and kneading) the above-mentioned components by using an agitator such as a three-roll mill, a ball mill, and a sand mill, and by filtering the components through a filter such as a 5 μm-membrane filter, if necessary.

<<Cell Culture Substrate>>

A cell culture substrate may take any shapes, sizes, and the like without limitation, as long as it is formed using the above-mentioned photosensitive resin composition.

The cell culture substrate preferably has a glass-transition temperature (Tg) higher than 37° C. When Tg of the cell culture substrate is higher than 37° C., it is possible to suppress deformation or degradation of the cell culture substrate during cell culture. Tg of the cell culture substrate can be enhanced by increasing the cross-linking degree or molecular weight of materials constituting the cell culture substrate. Specifically, Tg of the cell culture substrate can be enhanced by increasing the contents of the polyfunctional monomer (A1) or the bifunctional monomer (A2) in the photosensitive resin composition, or increasing an exposure light amount when the photosensitive resin composition is cured by exposure to light. Furthermore, in the photopolymerizable monomer (A) in the photosensitive resin composition, in the case of a monomer having the same number of ethylenically unsaturated double bonds, when the content of monomers having high ratio of aromatic groups per molecular weight is increased, Tg of the cell culture substrate tends to be increased.

Furthermore, as mentioned above, the cell culture substrate may have a cell culture surface provided with a concave-convex pattern.

<<Method for Manufacturing Cell Culture Substrate>>

A method for manufacturing a cell culture substrate is not particularly limited as long as the method can cure the above-mentioned photosensitive resin composition by exposure to light, and form a cell culture substrate having a desired shape. A preferable method for manufacturing a cell culture substrate includes:

applying a photosensitive resin composition for forming a cell culture substrate so as to form a coating film on a base plate; and exposing the coating film on the base plate to light so as to cure the coating film. The above-mentioned method for manufacturing a cell culture substrate may include peeling off the exposed coating film from the base plate, if necessary, after the coating film on the base plate is cured by exposure to light.

The base plate on which the photosensitive resin composition is to be applied in the applying is not particularly limited as long as it is not deformed or degraded while manufacturing a cell culture substrate. As mentioned above, the cell culture substrate may have a surface provided with a concave-convex pattern. On the surface on which the photosensitive resin composition is to be applied, when a base plate provided with a concave-convex pattern serving as a mold corresponding to the concave-convex pattern of the cell culture substrate is used, it is possible to form a cell culture substrate having a surface provided with a concave-convex pattern.

In this method, when the photosensitive resin composition contains a photopolymerizable monomer (A) including a predetermined amount of polyfunctional monomer (A1) having tri- or more-functionality, a concave-convex pattern serving as a mold provided to a base plate is accurately transferred to the coating film of the photosensitive resin composition, and a cell culture substrate having a surface provided with a concave-convex pattern in desired shapes can be formed.

The shape of the concave-convex pattern of the cell culture substrate is not particularly limited as long as cells can be favorably cultured. Examples of the concave-convex pattern which may be provided on the cell culture substrate include a line-and-space pattern composed of a line as a convex part and space as a concave part, a hole pattern including a plurality of holes as concave parts, a dot pattern including a plurality of columnar or prismatic convex parts, etc. Such a pattern on the surface of the base plate can be formed by, for example, applying a photoresist composition on the substrate for forming the base plate so as to form a coating film, then exposing the coating film to light through a mask having a desired pattern, and then, developing the exposed coating film.

Sizes of a concave part or a convex part in the concave-convex pattern are not particularly limited as long as cells can be favorably cultured. For example, in a line-and-space pattern, it is preferable that each of the width of the line and the width of the space is in the range of 5 to 5000 nm. Furthermore, in the line-and-space pattern, it is preferable that the depth of the space is in the range of 5 to 5000 nm.

The thickness of the cell culture substrate is preferably in the range of 10 nm to 100 μm. When the thickness of the cell culture substrate is in such a range, in particular, self-fluorescence of the cell culture substrate is easily suppressed. Therefore, use of the cell culture substrate having a thickness in such a range facilitates observation of cultured cells under a fluorescence microscope. Note here that when the cell culture substrate is provided with a concave-convex pattern on the cell culture surface thereof, the thickness of the cell culture substrate denotes a distance from a surface opposing the cell culture surface of the cell culture substrate to a surface of a convex part of the concave-convex pattern.

A method for forming the coating film on the base plate is not particularly limited, and examples of the method include a method of dropping a predetermined amount of the photosensitive resin composition onto the base plate, a method using contact-transfer type coating devices such as a roll coater, a reverse coater, and a bar coater, and a method using non-contact type coating devices such as a spinner (a rotary coater) and a curtain flow coater.

After the coating film is formed, it is preferable that a base plate having a coating film is placed under the reduced pressure conditions and the coating film is subjected to degassing.

A method for exposing the coating film to light in the exposing is not particularly limited as long as the curing of the coating film favorably proceeds. For exposure to light, light sources radiating ultraviolet ray, such as a high pressure mercury lamp, an extra-high pressure mercury lamp, a xenon lamp, and a carbon arc lamp can be used. The exposure light amount when the coating film is exposed to light is appropriately determined in consideration of composition of the photosensitive resin composition, film thickness of the coating film, and the like. Typically, the exposure light amount when the coating film is exposed to light is preferably 10 to 100000 mJ/cm$^2$, and more preferably 100 to 50000 mJ/cm$^2$.

The method for exposing the coating film to light is not particularly limited; however, it is preferable that the coating film is firstly exposed to light in the air so as to partially cure the coating film. This method can prevent the photosensitive resin composition from overflowing from the base plate in the exposure to light, and enables the coating film to be subsequently exposed to light in water. When a coating film is exposed to light in water without carrying out exposure to light in the air, the coating film may be dissolved in water. When the coating film is exposed to light in water after the coating film is exposed to light in the air, it is possible to reduce inhibition of radical polymerization with oxygen, and thus excellent cured film can be obtained.

Furthermore, it is preferable that the exposing includes exposing the coating film to light in a vacuum. When the exposing of the coating film to light in a vacuum is carried out, the coating film of the photosensitive resin composition can be cured in a state in which the coating film is in close contact with the base plate, so that a cell culture substrate having desired shapes can be easily formed. Furthermore, when the exposing of the coating film to light in a vacuum is carried out, it is also preferable that the exposing to light is carried out while a pressure is applied from the upper surface of the base plate. In this case, it is possible to cure the coating film of the photosensitive resin composition in a state in which the coating film is further in close contact with the base plate. When the exposing includes exposing to light in a vacuum, or exposing to light in a vacuum with pressure applied, in particular, when a base plate provided with a concave-convex pattern as a mold is used to form a cell culture substrate, the concave-convex pattern of the mold can be accurately transferred to the cell culture substrate. Exposing of the coating film to light under such conditions can suppress contraction when the photosensitive resin composition is cured, so that it is considered that the concave-convex pattern of the mold can be accurately transferred to the cell culture substrate.

Examples of the method for exposing the coating film to light in a vacuum include a method for exposing the coating film to light in a vacuum after the surface of the coating film is covered with film such as a PET film, and then exposing the coating film to light in a state in which at least a portion between the film and the coating film is made to be in a vacuum. Examples of the method of exposure to light in a vacuum with pressure applied include a method such as negative pressure exposure to light.

The coating film which has been cured by exposure to light by the method as described above is used as a cell culture substrate after it is peeled off from the base plate, as needed.

Furthermore, it is preferable that the coating film which has been cured by exposure to light is subjected to plasma treatment. When the cured coating film is subjected to plasma treatment, it is possible to form a cell culture substrate to which cells can be easily attached. Plasma to be used for the plasma treatment is not particularly limited as long as desired effect can be obtained, and preferable examples thereof include $O_2$ plasma, $N_2$ plasma, and $CF_4$ plasma, and the like. The timing at which the plasma treatment is carried out is not particularly limited, and the plasma treatment can be carried out at any timing before or after the cured coating film is peeled off from the base plate.

Furthermore, it is preferable that the cell culture substrate which has been peeled off from the base plate is rinsed with a rinsing liquid. By rinsing the cell culture substrate with a rinsing liquid, compounds such as unreacted photopolymerizable monomer (A) and photopolymerization initiator (B), which may cause cytotoxicity, may be removed from the surface of the cell culture substrate. Examples of preferable rinsing liquid include organic solvents such as propylene glycol-1-methyl ether acetate (PGMEA), isopropyl alcohol (IPA), and acetone, and water, and the like.

As mentioned above, the thickness of the cell culture substrate is preferably in the range of 10 nm to 100 μm. When the thickness of the cell culture substrate is in such a range, the strength of the cell culture substrate which has been peeled off from the base plate may be insufficient. In this case, the strength of the cell culture substrate can be compensated by bringing a disk or a film as a support into contact with a surface opposite to the cell culture surface of the cell culture substrate for supporting the cell culture substrate. As a material for the support, a transparent low self-fluorescent substance is preferable since it facilitates observation of cultured cells under a fluorescence microscope. Preferable examples of the transparent low self-fluorescence substance include glass, polyethylene terephthalate, polycarbonate, a cycloolefin polymer, polydimethylsiloxane, and polystyrene.

When the base plate to be used for formation of the cell culture substrate is a base plate selected from glass, polyethylene terephthalate, polycarbonate, a cycloolefin polymer, polydimethylsiloxane, or polystyrene, by using a cell culture substrate as a support for the cell culture substrate without peeling off the cell culture substrate from the base plate, it is possible to use the cell culture substrate as a cell culture substrate supported by the support.

EXAMPLES

Hereinafter, the present invention will be explained more specifically by way of Examples; however, the present invention is not limited to these Examples.

Examples 1 to 7 and Comparative Examples 1 to 4

In the Examples and Comparative Examples, the following polyfunctional monomers (A1), bifunctional monomers (A2), and monofunctional monomer (A3) were used.
[Polyfunctional Monomer (A1)]
P1: Trimethylolpropane triacrylate
P2: Dipentaerythritol hexaacrylate
P3: Reaction product of pentaerythritol triacrylate and toluene diisocyanate

[Bifunctional Monomer (A2)]
B1: Ethoxylated bisphenol A dimethacrylate (EO addition amount: 2.6 mol)
B2: Tetraethylene glycol diacrylate
[Monofunctional Monomer (A3)]
M1: Phenol EO-added acrylate (EO-added amount: 2.0 mol)

Furthermore, in the Examples and Comparative Examples, the following photopolymerization initiators (B) were used. PI1: α-aminoalkylphenone-based photopolymerization initiator, 2-methyl-1-[4-(methylthio)phenyl]-2-morpholinopropan-1-one PI2: oxime ester-based photopolymerization initiator, ethanone, 1-[9-ethyl-6-(2-methyl benzoyl)-9H-carbazol-3-yl], 1-(o-acetyloxime)

A photosensitive resin composition of each of the Examples 1 to 7 and Comparative Examples 1 to 4 was obtained by homogeneously mixing photopolymerizable monomer (A) and photopolymerization initiator (B) of types and in amount described in Table 1.

(Cytotoxicity Test)

A cell culture substrate having a smooth cell culture surface was produced according to the following method using the photosensitive resin composition of each of the Examples 1 to 7 and Comparative Examples 1 to 4. A cell culture test was carried out according to the following method using the obtained cell culture substrate, and the cytotoxicity of each base plate was evaluated. Evaluation results of the cytotoxicity test of the photosensitive resin compositions of the Examples 1 to 7 and Comparative Examples 1 to 4 are shown in Table 1.

[Formation of Cell Culture Substrate]

A base plate obtained by curing a film formed by using ArF resist (TArF-6619 (manufactured by TOKYO OHKA KOGYO CO., LTD.)) was used as a base plate for forming a cell culture substrate. A coating film of the photosensitive resin composition was formed on the base plate by dropping 0.5 ml each of photosensitive resin composition of each of the Examples and Comparative Examples using a dropping pipette on a smooth surface of the aforementioned base plate which was cut in 3 cm×3 cm. Next, the base plate provided with a coating film of the photosensitive resin composition was placed under the depressurized conditions of 100 Pa for 30 min so that the coating film was degassed. The degassed coating film was exposed to light in an exposure light amount of 999 mJ/m$^2$ by using an ultraviolet ray irradiation device (HMW-532D manufactured by ORC Co., Ltd.) in the air. Thereafter, in a vacuum, exposure to light in an exposure light amount of 999 mJ/m$^2$ was repeated five times to cure the coating film by using an ultraviolet ray irradiation device (HMW-532D manufactured by ORC Co., Ltd.). The cured coating film was peeled off from the base plate, followed by soaking the cured coating film in PGMEA for 10 min so as to rinse thereof, and spraying nitrogen gas to the cured coating film and drying thereof. The dried cured coating film was subjected to $O_2$ plasma treatment using a plasma treatment device (TCA-3822, manufactured by TOKYO OHKA KOGYO CO., LTD.) under the conditions of pressure of 40 Pa, temperature of 40° C., output power of 50 W, treatment time of 20 seconds, and oxygen flow rate of 200 ml/min so as to obtain a cell culture substrate.

A cell culture substrate obtained in each of the Examples and Comparative Examples was cut into an 8 mm×8 mm section, and the section was placed in a well of 24-well cell culture plate. Then, the plate with the section of the cell culture substrate mounted was treated with ethylene oxide gas (EOG) at 40° C. for 22.5 hours. After treatment with EOG, the plate was placed in a vacuum (100 torr) for 24 hours. Then, mouse osteoblast-like cells MC3T3-E1 together with 800 µl of MEMα medium (manufactured by Wako Pure Chemical Industries, Ltd.) were seeded so that the number of cells reached 2×10⁴ cells for each well. After the cells were seeded, they were subjected to incubation at 37° C. for 72 hours. Then, the inside of the well was washed with 1 ml of PBS (phosphate buffered saline) twice, and then a cytotoxicity test was carried out using an agent for counting the number of living cells (Cell Count Reagent SF (manufactured by NACALAI TESQUE, INC.)). After 300 µl of MEMα medium and 15 µl of Cell Count Reagent SF were placed in each well, they were incubated at 37° C. for one hour. Then, 100 µl each of MEMα medium including Cell Count Reagent was harvested from each well of the cell culture plate. The harvested sample was filled into a well of a 96-well micro-plate corresponding to the microplate reader. Next, the microplate in which each sample was filled into the well was treated by using a microplate reader (VersaMax (manufactured by Molecular Devices)), and absorbance of each sample at wavelength 450 nm (ABS) was measured. Furthermore, a sample of the MEMα medium including a Cell Count Reagent obtained by carrying out culture using MEMα medium and culture using MEMα medium including a Cell Count Reagent by using a cell culture substrate made of polystyrene (manufactured by IWAKI Scitech) was obtained by the same manner as in Examples and Comparative Examples, and the absorbance ($ABS_{st}$) at wavelength 450 nm of each of the obtained samples was measured. The cytotoxicity of the cell culture substrates of Examples and Comparative Examples were evaluated as the cytotoxicity of the cell culture substrate made of polystyrene was defined as a reference. Specifically, the cytotoxicity of the cell culture substrate of each of Examples and Comparative Examples was evaluated based on the values of $ABS/ABS_{st}$ according to the following criteria. Note here that the value of $ABS_{st}$ was 0.35.

"Good" (low cytotoxicity): value of $ABS/ABS_{st}$ is 0.5 or more.

"Bad" (high cytotoxicity): value of $ABS/ABS_{st}$ is less than 0.5.

Examples 1 to 7 show that, when a photosensitive resin composition including a photopolymerizable monomer (A) including 10% by mass or more of a polyfunctional monomer (A1) having tri- or more-functionality and a predetermined range of an amount of photopolymerization initiator (B) is used, a cell culture substrate capable of favorably culturing cells is obtained.

Comparative Examples 1 and 3 show that, when the photopolymerizable monomer (A) does not include the polyfunctional monomer (A1) having tri- or more-functionality, a cell culture substrate capable of favorably culturing cells cannot be easily obtained.

Comparative Examples 2 and 4 show that, when the content of the photopolymerization initiator (B) in the photosensitive resin composition is excessively small or large, a cell culture substrate capable of favorably culturing cells cannot be easily obtained.

(Pattern Transfer Property Test)

A cell culture substrate was formed by using photosensitive resin compositions of Examples 1 to 6, and Comparative Examples 1 to 4 in the same manner as in the cell culture substrate to be used for the cytotoxicity test, except that a base plate for forming cell culture substrate was changed to a base plate provided with a line-and-space pattern having a pattern depth of 60 µm and width of 30 µm on the surface thereof. A cross section of the obtained cell culture substrate was observed under a scanning electron microscope (SEM SU-8000, manufactured by Hitachi High-Technologies Corporation) to evaluate the pattern transfer property. A case where the pattern shape of the surface of the base plate was accurately transferred to the cell culture substrate was determined as "Good", and a case where the pattern shape of the surface of the base plate was not accurately transferred to the cell culture substrate was determined as "Bad". Evaluation results of the pattern transfer properties for the photosensitive resin compositions of Examples 1 to 6, and Comparative Examples 1 to 4 are shown in Table 2. Note here that the pattern transfer property of photosensitive resin composition of Example 7 was evaluated in Examples 9-1 to 9-8 mentioned later.

TABLE 1

| | | Examples | | | | | | | Comparative examples | | | |
|---|---|---|---|---|---|---|---|---|---|---|---|---|
| | | 1 | 2 | 3 | 4 | 5 | 6 | 7 | 1 | 2 | 3 | 4 |
| Composition of photopolymerizable monomer (parts by mass) | | | | | | | | | | | | |
| | P1 | 15 | 50 | 50 | 40 | 20 | 50 | 6 | — | 50 | — | — |
| | P2 | — | — | 50 | 40 | — | — | 9 | — | 50 | — | 20 |
| | P3 | — | — | — | — | 60 | — | — | — | — | — | — |
| | B1 | 85 | 50 | — | — | — | 50 | 85 | 100 | — | — | 80 |
| | B2 | — | — | — | 20 | 20 | — | — | — | — | — | — |
| | M1 | — | — | — | — | — | — | — | — | — | 100 | — |
| Amount of photopolymerization initiator (parts by mass) | | | | | | | | | | | | |
| | PI1 | 3 | 3 | 3 | 3 | 3 | — | 3 | 3 | 0.1 | 3 | 6 |
| | PI2 | — | — | — | — | — | 2 | — | — | — | — | — |
| Cytotoxicity | $ABS/ABS_{st}$ | 1.24 | 0.87 | 1.05 | 0.97 | 1.12 | 1.10 | 1.12 | 0.48 | 0.12 | 0.17 | 0.25 |
| | Evaluation | Good | Good | Good | Good | Good | Good | Good | Bad | Bad | Bad | Bad |

TABLE 2

| | Examples | | | | | | | Comparative examples | | | |
|---|---|---|---|---|---|---|---|---|---|---|---|
| | 1 | 2 | 3 | 4 | 5 | 6 | 7 | 1 | 2 | 3 | 4 |
| Composition of photopolymerizable monomer (parts by mass) | | | | | | | | | | | |
| P1 | 15 | 50 | 50 | 40 | 20 | 50 | 6 | — | 50 | — | — |
| P2 | — | — | 50 | 40 | — | — | 9 | — | 50 | — | 20 |
| P3 | — | — | — | — | 60 | — | — | — | — | — | — |
| B1 | 85 | 50 | — | — | — | 50 | 85 | 100 | — | — | 80 |
| B2 | — | — | — | 20 | 20 | — | — | — | — | — | — |
| M1 | — | — | — | — | — | — | — | — | — | 100 | — |
| Amount of photopolymerization initiator (parts by mass) | | | | | | | | | | | |
| PI1 | 3 | 3 | 3 | 3 | 3 | — | 3 | 3 | 0.1 | 3 | 6 |
| PI2 | — | — | — | — | — | 2 | — | — | — | — | — |
| Pattern transfer property test | Good | Good | Good | Good | Good | Good | — | Bad | Good | Bad | Good |

Examples 1 to 6 show that, when a photosensitive resin composition including a photopolymerizable monomer (A) including 10% by mass or more of a polyfunctional monomer (A1) having tri- or more-functionality and a predetermined range of an amount of photopolymerization initiator (B) is used, a cell culture substrate having a surface provided with a fine concave-convex pattern can be easily formed.

Comparative Examples 1 and 3 show that, when the photopolymerizable monomer (A) does not include the polyfunctional monomer (A1) having tri- or more-functionality, it is difficult to form a cell culture substrate having a surface provided with a fine concave-convex pattern.

Note here that a cell culture substrate was manufactured by using the photosensitive resin compositions of Examples 1 to 6 and a base plate provided with a line-and-space pattern having a pattern depth of 150 nm and width of 75 nm, and the pattern on the base plate was favorably transferred to the cell culture substrate.

Example 8

A cell culture substrate for cytotoxicity test and a cell culture substrate for a pattern transfer property test were formed by using the photosensitive resin composition of Example 1 in the same manner as in Example 1, except that the exposure conditions were changed to the condition in which exposure in an exposure light amount of 999 mJ/m$^2$ in the air was repeated five times. The obtained cell culture substrate was evaluated for the cytotoxicity and the pattern transfer property by the above-mentioned method. The results of the cytotoxicity test are shown in Table 3 and the results of the pattern transfer property test are shown in Table 4.

Examples 9-1 to 9-8

A cell culture substrate for cytotoxicity test and a cell culture substrate for a pattern transfer property test were formed in the same manner as in Example 1, except that following the exposure in an exposure light amount of 999 mJ/m$^2$ in the air, exposure in an exposure light amount described in Table 2 in water was carried out, and then exposure in an exposure light amount described in Table 2 in vacuum, as well as the photosensitive resin composition of Example 7 was used. The obtained cell culture substrate was evaluated for cytotoxicity and pattern transfer property by the above-mentioned method. The results of the cytotoxicity test are shown in Table 3 and the results of the pattern transfer property test are shown in Table 4.

TABLE 3

| | | Examples | | | | | | | | |
|---|---|---|---|---|---|---|---|---|---|---|
| | | 8 | 9-1 | 9-2 | 9-3 | 9-4 | 9-5 | 9-6 | 9-7 | 9-8 |
| Exposure light amount in water (mJ/cm$^2$) | | 0 | 200 | 500 | 1000 | 2000 | 3000 | 4000 | 5000 | 5000 |
| Exposure light amount in a vacuum (mJ/cm$^2$) | | 0 | 5000 | 5000 | 5000 | 5000 | 5000 | 5000 | 5000 | 0 |
| Cytotoxicity | ABS/ABS$_{st}$ | 1.01 | 0.98 | 1.05 | 1.21 | 1.10 | 1.02 | 1.06 | 1.12 | 1.06 |
| | Evaluation | Good | Good | Good | Good | Good | Good | Good | Good | Good |

Example 8 and Examples 9-1 to 9-8 show that, when a photosensitive resin composition including a photopolymerizable monomer (A) including 10% by mass or more of a polyfunctional monomer (A1) having tri- or more-functionality and a predetermined range of an amount of photopolymerization initiator (B) is used, a cell culture substrate capable of favorably culturing cells can be formed regardless of exposure methods.

TABLE 4

| | Examples | | | | | | | | |
|---|---|---|---|---|---|---|---|---|---|
| | 8 | 9-1 | 9-2 | 9-3 | 9-4 | 9-5 | 9-6 | 9-7 | 9-8 |
| Exposure light amount in water (mJ/cm$^2$) | 0 | 200 | 500 | 1000 | 2000 | 3000 | 4000 | 5000 | 5000 |
| Exposure light amount in a vacuum (mJ/cm$^2$) | 0 | 5000 | 5000 | 5000 | 5000 | 5000 | 5000 | 5000 | 0 |
| Pattern transfer property test | Bad | Good | Good | Good | Good | Good | Good | Good | Bad |

Examples 9-1 to 9-7 show that, when the exposing include exposure to light in a vacuum, the transfer property of the pattern are not influenced by exposure to light in water. On the other hand, Example 8 and Example 9-8 show that, even when exposure to light is carried out in a sufficient exposure light amount in the air or in water, when the exposure to light is not carried out in a vacuum, the pattern on the base plate serving as a mold is difficult to be accurately transferred to the cell culture substrate.

The invention claimed is:

1. A cell culture substrate comprising a cured product of a photosensitive resin composition for forming a cell culture substrate, wherein the photosensitive resin composition for forming a cell culture substrate comprises a photopolymerizable monomer (A) and a photopolymerization initiator (B), wherein the photopolymerizable monomer (A) includes 10% by mass or more of a polyfunctional monomer (A1) having tri- or more-functionality in relation to a mass of the photopolymerizable monomer (A) and a bifunctional monomer (A2), a content of the photopolymerization initiator (B) is 0.5 to 5.0% by mass in relation to a mass of the photosensitive resin composition, and the bifunctional monomer (A2) is a compound having the following formula 1:

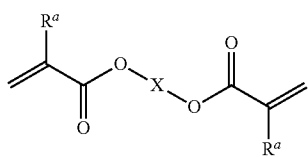
(1)

wherein R$_a$ each independently represents a hydrogen atom, or an alkyl group having 1 to 5 carbon atoms; X represents a divalent group expressed in the following formula 2:

$$-(C_2H_4O)_k-(C_3H_6O)_l-(Y)_j-(C_2H_4O)_m-(C_3H_6O)_n- \quad (2)$$

wherein Y is a group selected from divalent groups expressed in the following formulae Y1 to Y3:

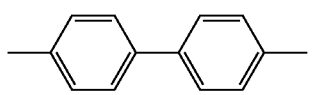
(Y1)

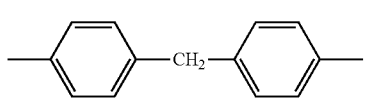
(Y2)

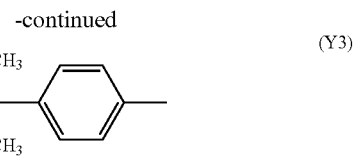
(Y3)

wherein k, l, m, and n each independently represents an integer of 0 or more; a sum of k, l, m, and n is an integer of 2 to 6; and j represents 1.

2. The cell culture substrate according to claim 1, wherein a glass-transition temperature (Tg) is higher than 37° C.

3. The cell culture substrate according to claim 2, wherein the cell culture substrate is supported by a support that is in contact with a surface opposite to a cell culture surface of the cell culture substrate, and the support is a disk or a film made of glass, polyethylene terephthalate, polycarbonate, a cycloolefin polymer, polydimethylsiloxane, or polystyrene.

4. The cell culture substrate according to claim 1, further comprising a surface provided with a concave-convex pattern.

5. The cell culture substrate according to claim 1, wherein a thickness thereof is 10 nm to 100 μm.

6. A method for manufacturing a cell culture substrate, the method comprising:
applying a photosensitive resin composition for forming a cell culture substrate according to claim 1 so as to form a coating film on a base plate; and
exposing the coating film to light so as to cure the coating film.

7. The method for manufacturing a cell culture substrate according to claim 6, the method further comprising peeling off the exposed coating film from the base plate.

8. The method for manufacturing a cell culture substrate according to claim 7, the method further comprising rinsing the exposed coating film, which has been peeled off in the peeling, with a rinsing liquid.

9. The method for manufacturing a cell culture substrate according to claim 6, further comprising plasma treatment for irradiating the exposed coating film with plasma.

10. The method for manufacturing a cell culture substrate according to claim 6, wherein the base plate has a surface provided with a concave-convex pattern.

11. The method for manufacturing a cell culture substrate according to claim 6, wherein the exposing includes exposure to light in a vacuum.

12. The method for manufacturing a cell culture substrate according to claim 11, wherein the exposing includes exposure to light in a vacuum in a condition in which a pressure is applied to the coating film from an upper surface of the base plate.

13. The cell culture substrate according to claim 1, wherein the polyfunctional monomer (A1) is a (meth)acrylate compound.

14. The cell culture substrate according to claim 1, wherein the photosensitive resin composition does not comprise a monofunctional monomer.

15. The cell culture substrate according to claim 1, wherein the photopolymerization initiator (B) comprises an oxime ester-based photopolymerization initiator.

* * * * *